(12) United States Patent
Engebretsen et al.

(10) Patent No.: US 6,420,882 B1
(45) Date of Patent: Jul. 16, 2002

(54) APPARATUS FOR CAPACITIVE ELECTRICAL DETECTION

(75) Inventors: Bjørn Engebretsen, Oppegård; Jon Morten Halleraker, Oslo, both of (NO)

(73) Assignee: Sentech AG, Trollasen (NO)

( * ) Notice: Subject to any disclaimer, the term of this patent is extended or adjusted under 35 U.S.C. 154(b) by 0 days.

(21) Appl. No.: 09/402,635

(22) PCT Filed: Apr. 6, 1998

(86) PCT No.: PCT/NO98/00115
§ 371 (c)(1),
(2), (4) Date: Nov. 12, 1999

(87) PCT Pub. No.: WO98/45672
PCT Pub. Date: Oct. 15, 1998

(30) Foreign Application Priority Data

Apr. 8, 1997 (NO) ................................................. 971615

(51) Int. Cl.$^7$ ............................................... G01R 27/26
(52) U.S. Cl. ....................................................... 324/667
(58) Field of Search ................................ 324/667, 678, 324/658, 679, 672, 601, 640, 684, 685, 690; 340/870.37; 331/176, 179, 65, 117 R (56) References Cited

U.S. PATENT DOCUMENTS

| | | | |
|---|---|---|---|
| 3,805,185 A | * 4/1974 | Kishi | 331/65 |
| 4,399,404 A | * 8/1983 | Resh | 324/61 R |
| 5,117,206 A | * 5/1992 | Imamura | 331/158 |
| 5,777,482 A | * 7/1998 | Tielert et al. | 324/678 |

FOREIGN PATENT DOCUMENTS

| | | |
|---|---|---|
| DE | 1 773 448 | 9/1971 |
| DE | 25 24 608 | 12/1975 |
| DE | 25 32 564 | 2/1977 |
| EP | 0 077 595 | 4/1983 |
| GB | 1 392 708 | 4/1975 |
| GB | 2 066 961 | 7/1981 |
| GB | 2 074 325 | 10/1981 |
| GB | 2 256 489 A | 12/1992 |
| NO | 139983 | 3/1979 |

OTHER PUBLICATIONS

Paul Horowitz, Winfield Hill, Measurements and Signal Process, The Art of Electronics, pp. 1002–1004, Apr. 23, 1991.

Ramon Pallas–Arney, John G. Webster, Reactance Variation and Electromagnetic Sensors, Sensors and Signal Conditioning, pp 140–149, John Wiley & Sons, Inc. Mar. 12, 1992.

* cited by examiner

Primary Examiner—N. Le
Assistant Examiner—Etienne P LeRoux
(74) Attorney, Agent, or Firm—Cohen, Pontani, Lieberman & Pavane (57) ABSTRACT

Apparatus for capacitive electrical detection or measurement relating to a medium, comprising at least one electrode having a given surface extension and an oscillator circuit the output frequency of which is a function of the capacitance being associated with the electrode and the dielectric constant of the medium, and is taken as a basis for the detection or measurement. The effective spacing of the electrode from a counter electrode or from earth is of the same or a substantially higher order of magnitude as seen in relation to the surface extension of the electrode. A conductor connecting the electrode to the oscillator circuit has a length that is a small fraction as seen in relation to the surface extension of the electrode.

43 Claims, 9 Drawing Sheets

APPARATUS FOR CAPACITIVE ELECTRICAL DETECTION

The invention relates to an apparatus for capacitive electrical detection or measurement with respect to a medium, substance, material or object in a solid or fluid form. In many practical applications the media of interest comprise water, e.g. in the form of moisture in the substance or material concerned.

The apparatus is of the type comprising at least one electrode having a given surface extent and an oscillator circuit the output frequency of which is a function of the capacitance being associated with the electrode and the dielectric constant of the medium, and taken as a basis for the detection or measurement. The measurement principle is well known per se, as will appear e.g. from the book "Instrumenteringsteknikk" by Odd Arild Olsen, Tapirs forlag, 1988, pages 141 and 245. Examples of specific applications are given in McGraw-Hill Encyclopedia of Science & Technology, $7^{th}$ addition, volume 10, page 35 and volume 14, page 278.

There exist various earlier practical proposals and applications based on the known principle, where there is provided a capacitor in a relatively conventional sense, usually with plate-shaped electrodes between which there is received a dielectric in the form of the medium, substance or material concerned, that is subject to detection or measurement. In this connection there is reason to note that different media can have rather different dielectric constants, e.g. water having the value 80, oil the value 3 and air the value 1.

The object of this invention is to provide a novel apparatus being based upon the above principle, but having substantially expanded fields of application as well as an increased accuracy and sensitivity, as it is required when measuring e.g. pollution or moisture and likewise in demanding level measurements. As regards detection or measurement of pollution there can e.g. be the question of oil in water or water in oil. Also when level measurement is concerned the two media water and oil are of much interest in this connection.

As will appear from the following description there is here the question of detecting or measuring very small capacitance changes, and as explained in the following description it is a particular purpose to make possible exact measurement when such small capacitance changes occur. In this connection it has decisive significance that sources of error being present, are taken into account, such as temperature variations in the dielectric constant of water.

On this background and taking as a starting point an apparatus of the type mentioned at the beginning of this description, the novel and specific features according to the invention in the first place consist therein that the effective spacing of the electrode from a counter-electrode or from ground is of similar or substantially higher order of magnitude as seen in relation to the surface extent of the electrode, and that a conductor connecting the electrode to the oscillator circuit has a length that is a small fraction as seen in relation to surface extent of the electrode. More closely defined this involves in other words that the connecting conductor essentially represents a capacitance that is substantially smaller than the capacitance of the electrode.

In some embodiments according to the invention there will be incorporated a counter-electrode in the apparatus itself, whereas other embodiments do not comprise such a counter-electrode or another electrode in the apparatus, so that the environment or "ground" will act as a "counter-electrode". In all cases there is here the question of a form of "capacitor" that is fundamentally different from a capacitor in the usual sense. This is seen in the first place therein that here there is the question of a very "open" configuration where, in contrast to what applies to common capacitors, there does not exist any relatively small or directly measurable distance between two electrode plates, the surface extent or area of which is regularly of a substantial magnitude as seen in relation to the electrode or plate spacing. The apparatus according to the invention involves so to speak an inverted relationship between the effective spacing mentioned and the surface extent of the electrode. These geometrical relationships or dimensional relations will appear more closely from the exemplary embodiments described below with reference to the drawings. The same applies to the condition that the length of the conductor connection between the electrode and the oscillator circuit as mentioned, is very small compared to the surface extent of the electrode. Whereas the dimensions of the electrode in most embodiments as a rule can be reasonably measured in centimetres, the connecting conductor typically has a length that most suitably can be measured in millimetres, such as from a couple of millimetres up to a maximum or perhaps 10 millimetres.

As regards the capacitance relationship mentioned, i.e. between the connecting conductor and the actual electrode, it is to be noted additionally that the relationship applies both when the medium concerned influences the capacitance and when only air is present.

An additional factor associated with the particular electrode configuration being here of basic interest, is that the medium, substance, material or object to be subjected to detection or measurement, must not necessarily be brought close to the electrode or a possible counter-electrode in the apparatus. In certain embodiments there is obtained a desired larger penetration depth in media of interest, by locating or conveying it at some distance from the electrode, so that the capacitive or electrostatic field will be influenced by a larger volume of the medium during the detection or measurement process. Thus, the measurement will be more representative of larger proportions of the volume or bulk of the medium.

Although oscillator circuits based on various principles can be employed in this context, it is preferred according to the invention to employ an LC-oscillator where there is incorporated an air core coil and a temperature-sensing element in good thermal contact with the air core coil, for temperature compensation of the oscillator circuit. This type of oscillator-has been found to be particularly stable and to have a small sensitivity to sources of error, whereby in particular temperature compensation has much interest in the apparatus according to the invention. It will also be possible then to generate a temperature measurement signal that as such can also be utilized for other purposes than the direct temperature compensation of the oscillator circuit as mentioned above. Such utilization can take place with advantage in a microprocessor or computer, e.g. a PC, that also receives the output frequency from the oscillator circuit. Subsequent to a suitable and desired processing of the signals in the microprocessor or the computer, this delivers a resulting detection or measurement signal that can then be conveyed to an alarm, recording or display device. Such devices can also comprise additional data processing for a favourable presentation or utilization.

As already mentioned above, measurements or detection of interest can in many cases comprise water or moisture in the medium or object concerned. In such applications it is preferred according to the invention that the fundamental frequency of the oscillator circuit is within the range 10–100 MHz, preferably between 15 and 30 MHz. At such a choice of fundamental frequency the apparatus will be particularly well adapted for a high sensitivity with respect to water content, which is related to the fact that the loss factor for water has a pronounced minimum at the frequencies mentioned. As known the loss factor in this connection represents quite a different effect from the dielectric constant as discussed above. As also mentioned the dielectric constant, in particular for water, is very temperature dependent and according to the invention it is possible to compensate also for this by means of suitable processing in the microprocessor or computer mentioned. For illustration it can be mentioned here that the dielectric constant for water is about 80 at a temperature of +25° C., whereas the value is about 40 at a temperature of +80° C.

Among the important features contributing to a high sensitivity and good measuring results by means of the apparatus according to the invention, there is involved an advantageous calibration of the oscillator frequency based upon at one hand air and preferably dry air as a dielectric for the electrode, and at the other hand preferably another calibration with water as a dielectric for the electrode. In embodiments where several separate electrodes are incorporated, e.g. when level measurement is contemplated, such frequency calibration will be performed individually for each separate electrode. In fact such calibration will also correct for variations in components or parameters of the oscillator circuits, so that the electrode and the associated oscillator circuit in this respect will be treated as an integral unit. As it will also appear from the following description, there can moreover according to the invention, be provided for a similar calibration process when the apparatus has been put into operation, in particular in form of a repeated and adaptive calibration procedure during the whole operational time or life time of the measuring apparatus. In particular in the case of such apparatus where there is incorporated a number of individual electrodes as mentioned above, calibration as discussed here will be important, since each electrode-oscillator probe initially can have varying properties or parameters with respect both to sensitivity and temperature coefficient as well as fundamental frequency. All such factors that vary from probe to probe in a complete plant or system, will be taken into account and corrected for during the calibration, that takes place by suitable programming of the microprocessor or computer.

This also comprises calibration or compensation for component aging in the oscillator circuit with time and changes in the properties of the electrodes, such as by coating that by and by can attach thereto, possibly in the form of fouling.

The above discussed, specific features according to the invention make it possible to provide apparatuses of the kind stated here, having a high sensitivity and a high accuracy in detection and measurement, as well as various and highly different applications that have not hitherto been possible in practice with known forms of capacitive detection or measurement. For example, it is possible to obtain measurements of as small a proportion as 0,1% of water in oil. Moreover, the apparatus according to the invention has the advantage of consuming very little electric power, namely at the order of magnitude of 1 mW in typical embodiments.

The invention as well as additional advantages and particular embodiments thereof, will be explained more closely in the following description with reference to the drawings, in which:

FIG. 9 shows a cross-sectional view of the apparatus of FIG. 8, FIG. 10 in block schematic form in a corresponding manner as FIG. 5, shows the electrical measurement system that can be employed in association with the apparatus of FIGS. 8 and 9, and FIG. 11 schematically shows an apparatus according to the invention for detection or measurement of flowing fluids.

Figure 1:
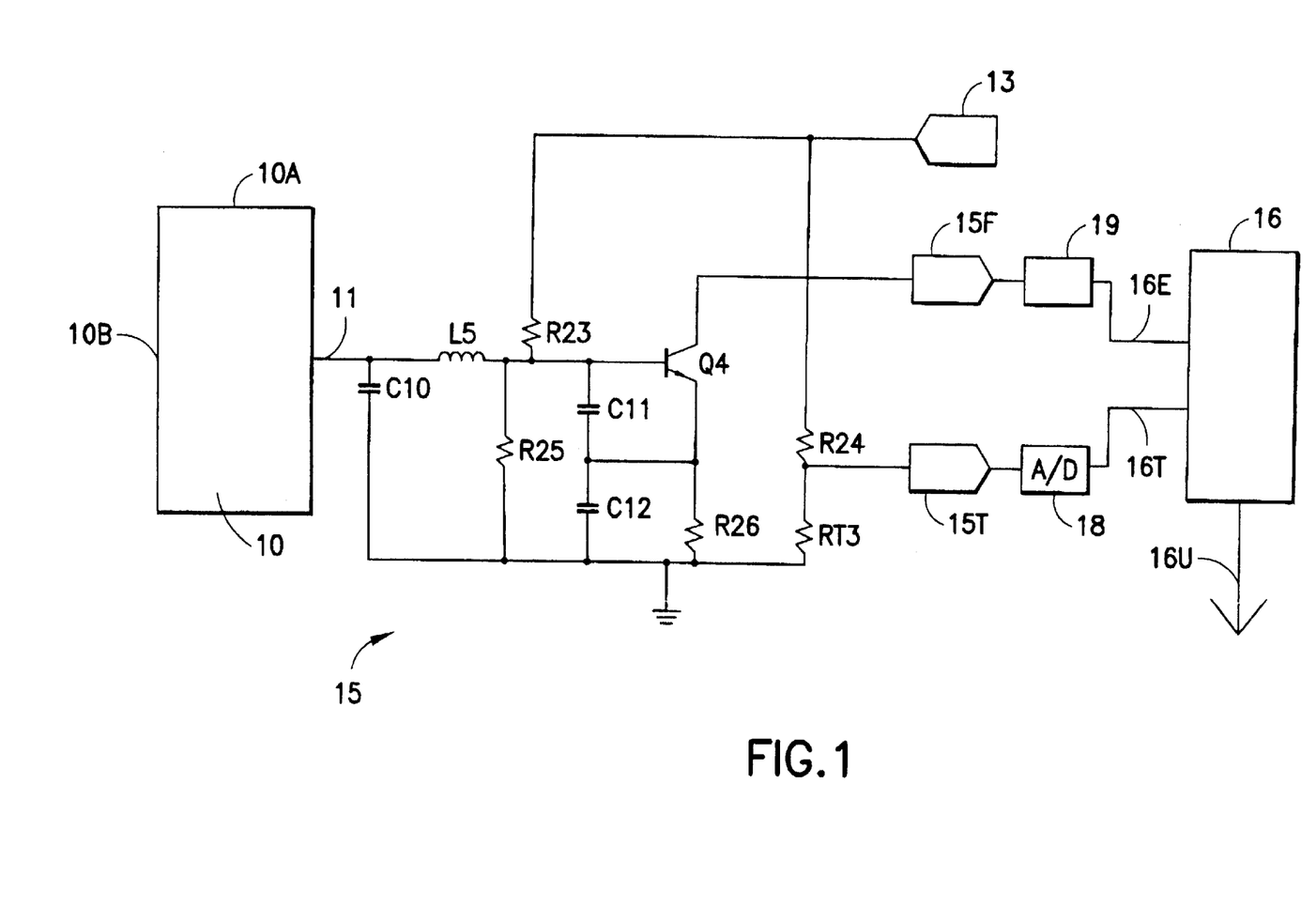
FIG. 1 shows an electrical circuit diagram in partial block form, according to an embodiment of the invention, FIG. 2 schematically shows an exemplary embodiment of an apparatus according to the invention being particularly intended for measurement of moisture in bulk goods or continuous materials, FIG. 3 in a corresponding schematic manner shows an embodiment particularly intended for measurement on a liquid or mass received in a measurement vessel.

In FIG. 1 the oscillator circuit is generally denoted 15, and it is seen that this is an LC oscillator. There is included an active component in the form of an NPN transistor Q4, whereas the frequency determining components in the first place consist of a coil L5 and a capacitor C10. In parallel to capacitor C10 there is the capacitance being represented by an electrode 10, which is shown here in rectangular plate shape as a typical design. The side edges of the electrode are denoted 10A and 10B, respectively. Coil L5 is an air core coil, i.e. without any other core material than air. This is a great advantage in view of the desired high stability being required in this connection. The capacitance of capacitor C10 shall be as constant as possible, whereas in contrast the capacitance being represented by the electrode 10 in parallel with capacitor C10, will vary depending upon the medium that may be present as a dielectric for electrode 10, namely in this case between the electrode and ground. In other words FIG. 1 does not show any other counter-electrode than ground with respect to electrode 10. This additional capacitance or measured capacitance being parallel to capacitor C10, will have an influence on the output frequency of the oscillator circuit, and it is this variation of the output frequency that is utilized for the intended detection or measurement.

Other components incorporated in oscillator circuit 15 are of conventional type and function, among other things for applying required operational voltages to transistor Q4, whereas in contrast component RT3 is a temperature-dependent resistor, such as a so-called NTC resistor. This is physically located in close thermal contact with air coil L5, primarily for the purpose of providing for temperature compensation in oscillator circuit 15, so that the output frequency thereof to the extent possible is independent of the ambient temperature. Accordingly one of a number of sources of error are eliminated to a substantial degree.

At 15F there is indicated an output unit for the oscillator frequency, that is converted in a following counter 19 to a digital signal that in turn is applied to an input 15F of a microprocessor or computer 16. Moreover from the temperature-dependent resistor RT3 there is taken a specific temperature measurement signal via an output unit 15T to an analog-digital converter 18 which through a second input 16T applies a corresponding digital signal to microprocessor 16. This, which can also be in the form of a more complete computer, such as a PC, performs a desired signal processing comprising, inter alia, necessary compensation for temperature-dependent inductance in air coil L5, as already mentioned. Upon this and possibly other types of signal processing in microprocessor 16, there is delivered a resulting detection or measurement signal 16U that can be conveyed to and utilized in an alarm, recording or display device. It is obvious that such devices may also comprise additional microprocessors or computers for the purpose of suitable processing or presentation for the end user.

At 13 there is shown an input unit that can serve for providing an activation signal to oscillator circuit 15 so that this enters into operation. Such activation or control has particular interest when the number of electrode-oscillator probes are included in a more complex apparatus or a measurement system, such as for level measurement. In such an apparatus each electrode normally will also have an associated and intimately related oscillator circuit.

The fundamental frequency of oscillator circuit 15 in actual practice will often be chosen in the MHz range, in particular when the medium, substance, material or object to be subjected to detection or measurement, contains water or moisture that is of interest, it is preferred according to the invention that the fundamental frequency is in the range 10–100 MHz, and preferably between 15 and 30 MHz. As previously mentioned water has a pronounced minimum in its loss factor within this range of frequencies.

Even though FIG. 1 is quite schematic and directed to the principle involved, it is seen that a lead 11 between electrode 10 and oscillator circuit 15, represented by the junction between capacitor C10 and coil L5, is very short and thus has a negligible capacitance as seen in relation to the capacitance of electrode 10 with respect to ground. This is essential according to the invention, and as an example of typical dimensional relationships the following is mentioned here: The surface of electrode 10 typically can be of dimensions 2×5 cm and the conductor lead 11 typically can have a length of 2 mm. More details regarding practical designs at this point can be found in the following description of embodiments illustrated in the other figures of drawings. In this connection it is also significant to note that in the actual oscillator circuit 15 the capacitance of the internal connections between the junction mentioned and the capacitor C10 and coil L5, respectively, has an influence on the output frequency. These connections however, can be kept quite short and stable in known ways, so that there is no risk of sources of error worth mentioning, as a consequence of these internal connections in oscillator circuit 15.

Figure 2:
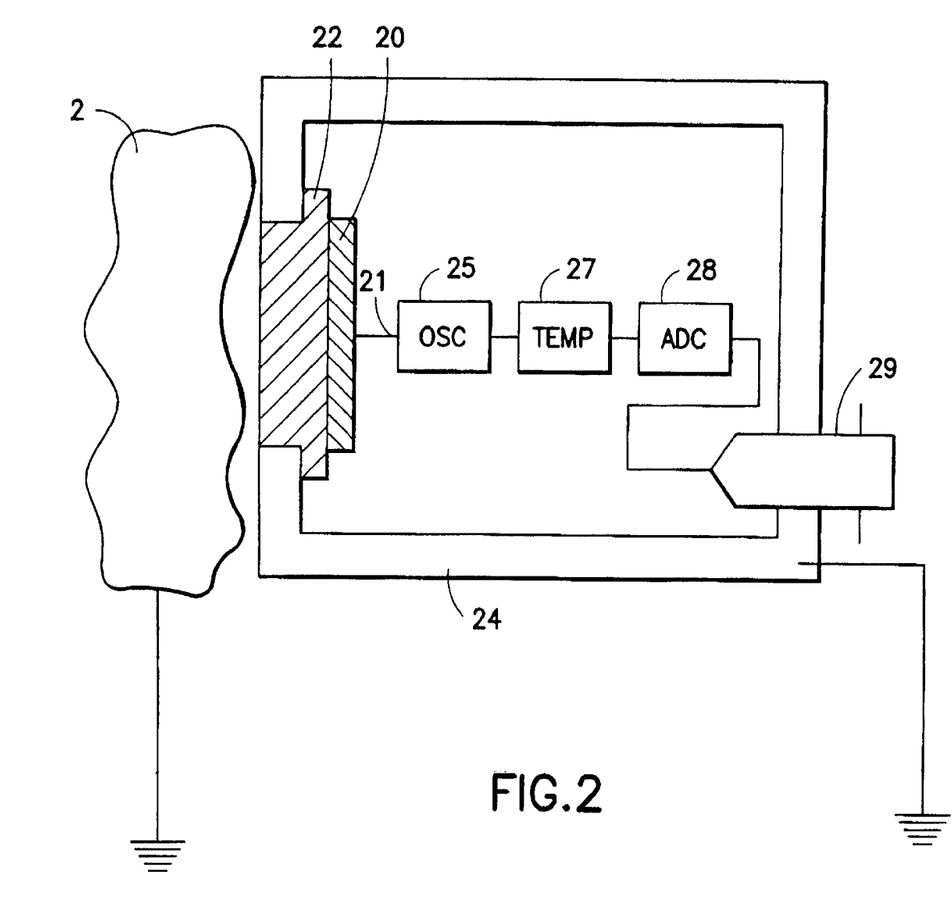

FIG. 2 shows an embodiment where a plate-shaped electrode 20 through a short conductor lead 21 cooperates with the actual oscillator circuit 25 having an associated temperature compensation circuit 27 and an analog-digital converter 28, is housed in an encapsulation or screen 24 of electrically conductive material. Output signals are taken through unit 29 that in similarity to the arrangement of FIG. 1, can lead to a microprocessor or computer for further signal processing and presentation.

An essential feature of the structure in FIG. 2 is a window 22 of electrically non-conductive material in one of the walls of encapsulation 24. Electrode 20 is applied to an internal surface of window 22, whereas the opposite and external surface thereof is adapted to be exposed to the surroundings, i.e. the region, space or position where the medium or object 2 concerned, is located or conveyed for the intended measurement or detection. In practice such an object will have a ground connection as indicated in the drawing. From the geometrical relationships apparent from FIG. 2 it is clear that object 2 to a substantial degree will influence the electrical field being due to electrode 20 when oscillator circuit 25 is activated. In addition to this effect with respect to ground, encapsulation 24 will here also to some degree play the role of a counter-electrode. It is seen however, that the effective distance from the surfaces of electrode 20 to adjacent portions of encapsulation 24, is relatively small or at least not dominating in relation to the dielectric effect due to the object 2. Likewise it is obvious that the capacitive influence of conductor 21 can be made negligible in the total picture or pattern of capacitances involved in such an embodiment. Specifically it is obvious that the capacitance of conductor 21 can not be significantly influenced by bodies or objects that otherwise more or less in random can occur or move in the vicinity of such a measuring apparatus.

The object 2 can represent material or goods the moisture in which is to be determined, and the apparatus of FIG. 2 can further in actual practice be adapted for measurement on continuous materials being passed by more or less continuously, such as in a paper machine. Depending upon the application concerned, it can be an advantage according to the invention that window 22 has dimensions of thickness being generally comparable to the surface extent of electrode 20, and can be larger than the wall thickness of enclosure 24. This contributes to the above mentioned favourable geometrical relationships for the purpose of avoiding varying stray capacitance effects.

As a purely practical matter and not the least as an advantageous embodiment with respect to function and manufacture, electrode 20 can be formed on one side of a circuit board, with the oscillator circuit provided essentially at the other side of the circuit board, so that the conductor lead 21 goes therethrough and therefore has a length corresponding to the thickness of the circuit board. Such an embodiment will be discussed more in detail with reference to FIG. 6 below. The length of conductor 21 then can be kept well below 5 mm, typically about 2 mm. As additional practical details it can be mentioned that window 22 suitably can be made of teflon, and that unit 29 can represent a coaxial cable or connection for a well screened delivery of output signals from the apparatus. Also the operational DC voltage for the circuits can be supplied through the same coaxial cable.

Although FIG. 2 does not in detail show the more closely integrated structure of oscillator circuit 25 with associated electronic circuits, in particular circuit 27 for temperature compensation, and electrode 20, it is obvious that these components can be assembled in such a manner that they have a relatively good thermal contact with object 2. The temperature of at least the adjacent surface of object 2 can then in many cases be sensed by the apparatus. In the embodiment of FIG. 2 the accuracy of such sensing will also depend on window 22. When in this manner the oscillator circuit has a good thermal contact with the medium, substance or material concerned, the output signals to the microprocessor can make it possible for the processor to correct also with respect to the temperature variation in the dielectric constant of the object, e.g. when there is a water content or moisture in object 2. Embodiments to be described in the following description can also be more favourable for the purpose of the correction discussed here.

Advantageously the embodiment of FIG. 2 as well as other embodiments described, can be subjected to frequency calibration in the first place with air as a dielectric for the electrode, and besides preferably with water as a dielectric. This form of calibration is suitably performed during the running production of such apparatuses, because component values and other factors usually will lead to individual variations, so that the nominal output frequency must be determined individually for each electrode-oscillator probe under standard conditions.

Figure 3:
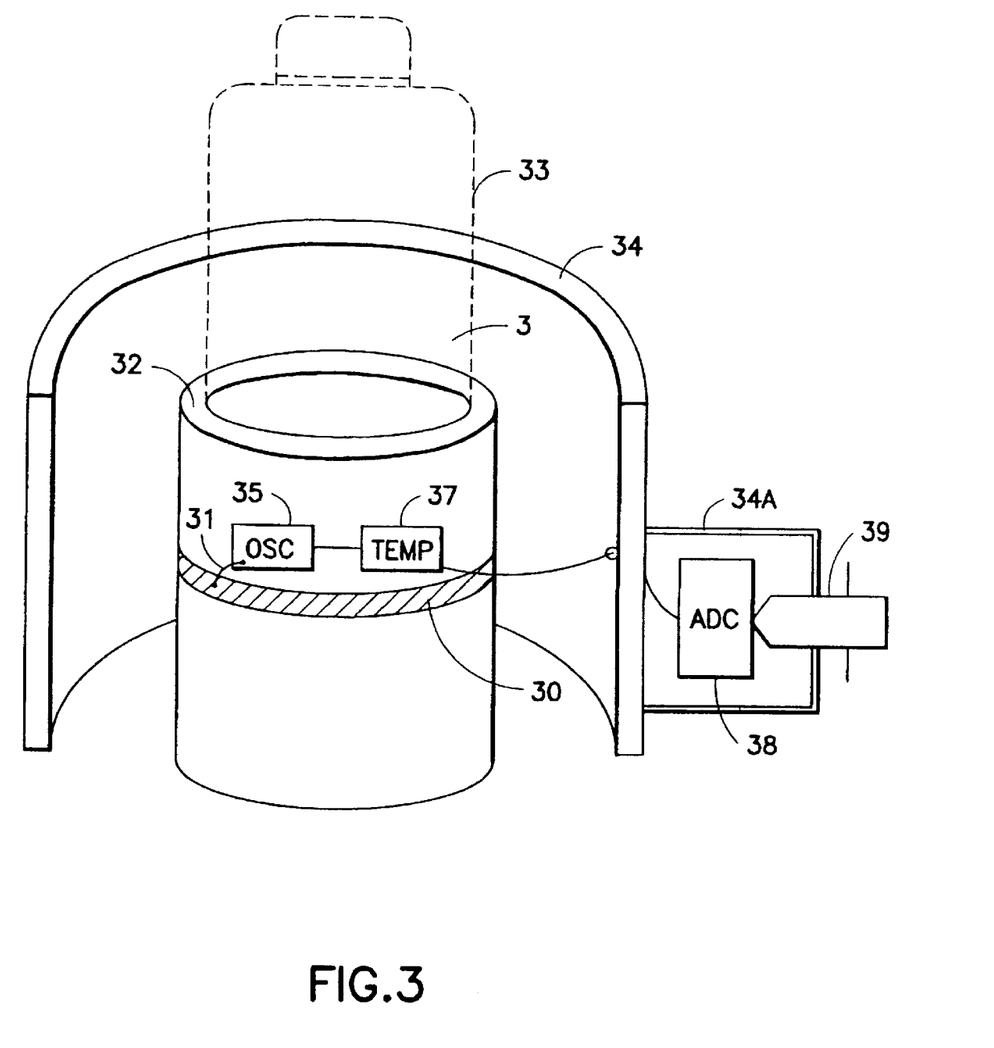

FIG. 3 shows an embodiment where a bottle-like measurement vessel 33 is adapted to receive a liquid or a mass to be subjected to measurement. Measuring vessel 33 can expediently be made of a plastic material. A cylindrical part 32 has an internal cavity for receiving the measuring vessel 33, and an electrode 30 in ribbon form is provided outside cylinder 32 around the circumference thereof. Accordingly, cylinder 32 consists of an electrically non-conductive material, such as teflon. When the measuring vessel 33 with a liquid or bulk goods filled in, has been introduced into cylinder 32, the electrode 30 will surround the measuring vessel at the level of the contents therein. Concentrically around cylinder 32 there is shown a screen 34 of electrically conductive material, e.g. aluminum. The geometrical relationships and dimensions are so chosen that the distance radially inwards from electrode 30 to the medium being subject to measurement, is much smaller than the radial distance outwards to screen 34. Nevertheless the capacitance between electrode 30 and screen 34 will be incorporated in the total capacitance that determines the oscillator frequency, namely as a parallel capacitance to that which exists radially inwards of electrode 30 in the cavity of cylinder 32, where the medium 3 in vessel 33 constitutes a dielectric. Depending on the properties of the medium this dielectric will represent a variable capacitance contribution that leads to variation in the output frequency of the oscillator and accordingly an output signal from the apparatus as in the embodiment of FIG. 2.

Relatively schematically in FIG. 3 there is indicated an oscillator circuit 35 having a short conductor lead 31 to electrode 30 and besides a temperature circuit 37 and an analog-digital converter 38. Circuit 38 in this case is located outside screen 34 in a screen box 34A which is also provided with an output connector 39 for e.g. a coaxial cable.

As mentioned above it is contemplated that the practical embodiment according to FIG. 3 can be based on a printed circuit board having the electrode 30 at one side and the oscillator circuit 35 with associated electronics at the other side. Circuit boards of such structure, that can be formed in an arcuate or circular ribbon-shaped configuration are available according to present-day technology.

Figure 4:
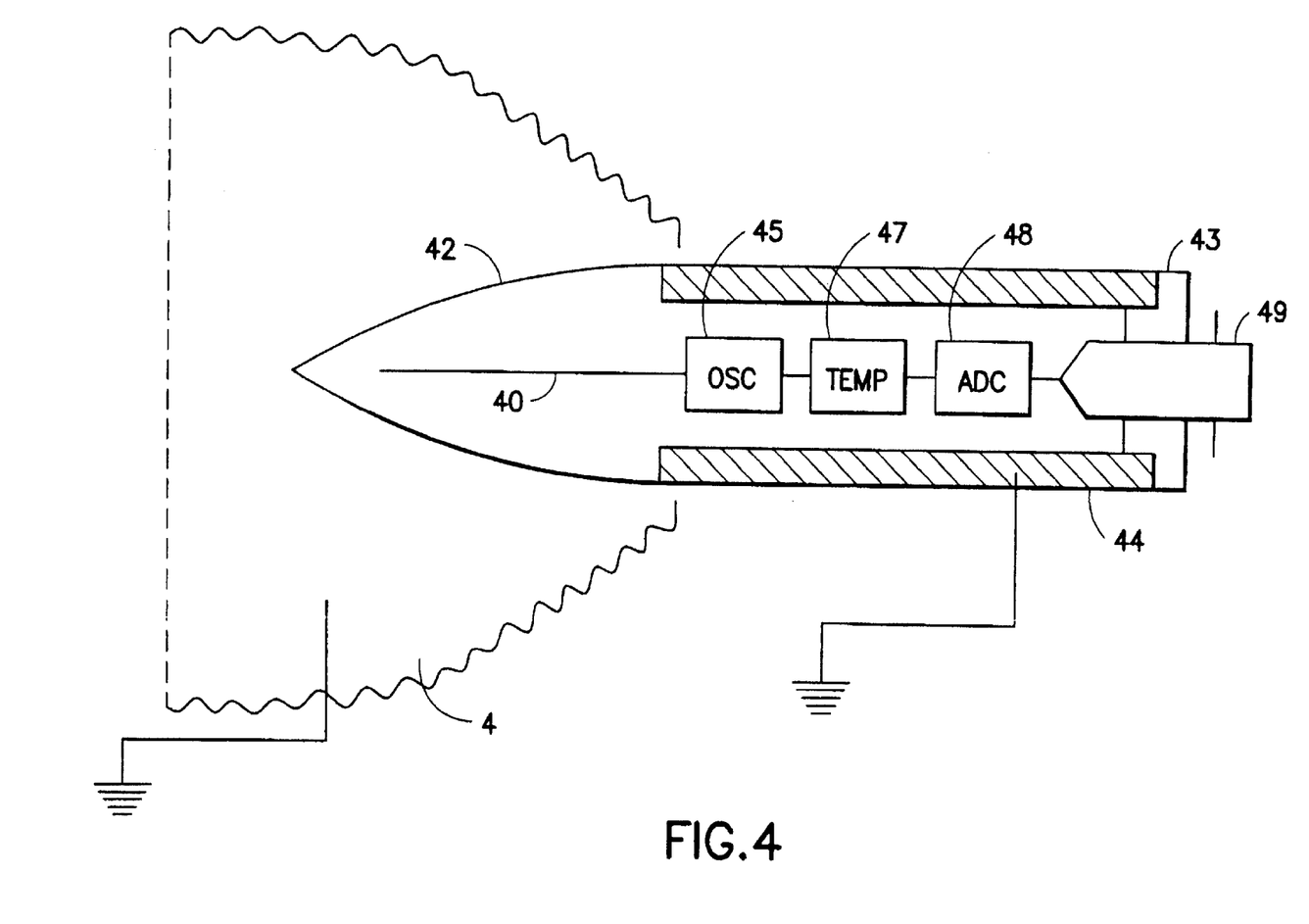
FIG. 4 shows an example of an apparatus in the form of a spear-like tool for measuring moisture in bulk goods.

In particular for measuring moisture in bulk goods there is shown a spear-like embodiment in FIG. 4. There is incorporated a rod- or thread-shaped electrode 40 which extends from oscillator circuit 45 forwardly in a front part 42 of the apparatus. Advantageously this front part is somewhat pointed in order to facilitate penetration into the bulk goods, that can be e.g. bales of collected waste, such as paper waste. Whereas the front part 42 mentioned, in the principle should consist of electrically non-conductive material, the remaining part of the tool is based on a surrounding enclosure 44 of tubular shape and consisting of an electrically conductive material, e.g. aluminium. This part therefore constitutes a screen for oscillator circuit 45 and an associated electronics circuit 47 for temperature compensation as explained previously, as well as an analog-digital converter 48. At the rear end of this tool there is shown a rear wall 43 with a lead-through for a coaxial connector unit 49. Also in this embodiment there can in part be considered to exist a form of counter-electrode, namely in the form of the screen enclosure 44. It is more essential however, that the object or bulk goods 4 being subject to measurement, to a high degree will have influence on the capacitance of electrode 4, among other things because the goods 4 as indicated, will normally have a good ground contact. In this case there is not at all any indication of a specific conductor lead between electrode 40 and oscillator circuit 45, since the electrode can extend directly up to a point of connection in the oscillator circuit itself.

When there is the question of measuring a liquid level in a tank or the like, it is highly relevant to employ a number of electrodes being located in a preferably vertical row in order that a varying liquid level can be detected or measured with a desired resolution. Such an embodiment is shown schematically in FIG. 5, where there are shown three such electrodes 50A, 50B and 50C. These electrodes are shown in the principle with a rectangular plate shape and with closely connected oscillators 55A, 55B and 55C, respectively. For each such electrode-oscillator probe there are taken out two leads as shown e.g. at 55T and 55F for electrode 50A. Thus, there is also here a frequency output signal 55F and a temperature output signal 55T, and correspondingly from the other two probes. For controlling or activating the probes according to a desired program or a measurement procedure, there are provided two selector circuits 51 and 52 for handling the frequency signals and the temperature signals respectively, and convey these to an output unit 56 with an associated connector 59 in similarity to the preceding exemplary embodiments. As in the preceding examples there is included for the temperature signals, an analog-digital converter 58 in the block diagram of FIG. 5.

Figure 5:
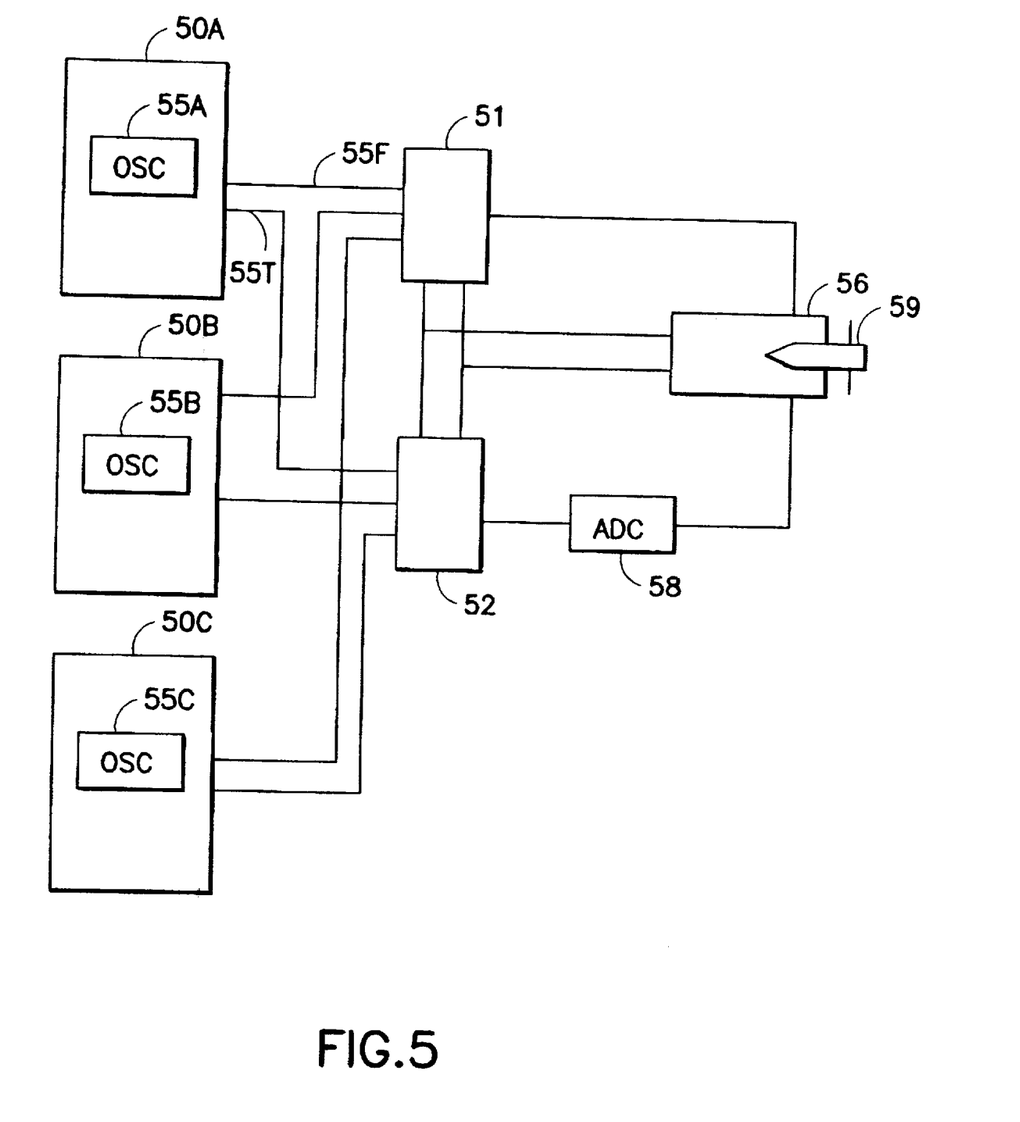
FIG. 5 shows a block diagram of an embodiment with three electrode-oscillator probes in a system, e.g. intended for level measurement, FIG. 6 in cross sectional view shows a level measurement apparatus based on a tubular structure, e.g. for the measurement of tank levels, such as at gasoline stations.

There is not shown any specific microprocessor or computer in FIG. 5, but unit 56 can possibly be considered to incorporate a microprocessor. A microprocessor or computer can particularly in such an embodiment be adapted to provide for frequency calibration with respect to the individual electrodes 50A, 50B, 50C having each an associated oscillator circuit, based on suitable programming of the microprocessor or computer, including the possibility of adaptive calibration or adjustment during the operational time of the apparatus. Such calibration can suitably be performed depending upon whether the electrode concerned is fully immersed in the liquid in question or is located as a whole above the liquid level. In most cases it will be simple to decide in an unambiguous way whether or not a given electrode is fully immersed.

Figure 6:
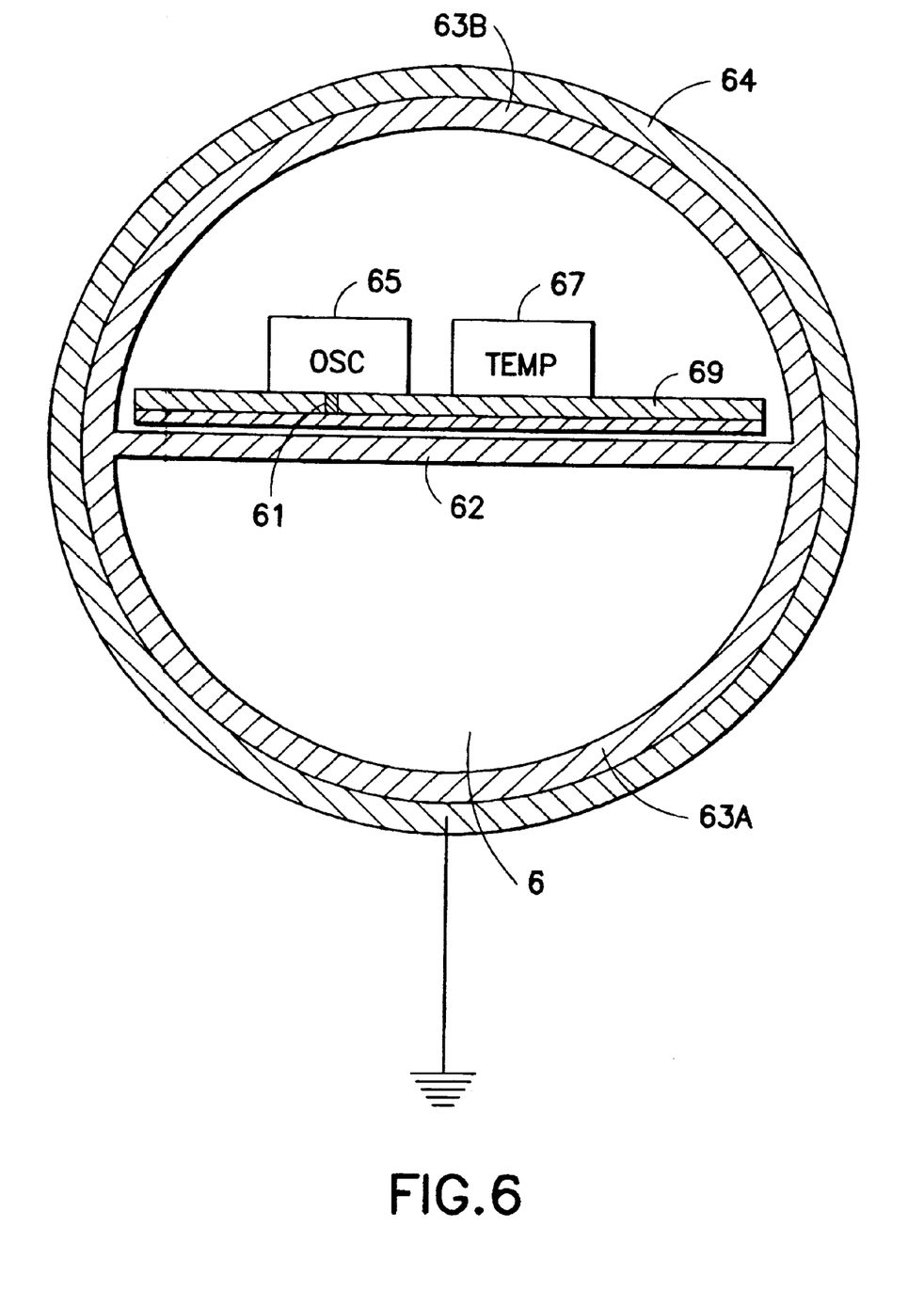

FIG. 6 shows an embodiment being developed particularly for measuring tank levels in gasoline stations and the like. For such purposes there is employed an arrangement having a vertical row of electrodes as in FIG. 5, but preferably with a still higher number of electrodes. The practical embodiment of FIG. 6 is shown in the form of a cross-section through a tubular structure adapted to be inserted down into and installed in a tank. Existing gasoline station tanks will often be equipped with vertical ducts or tubes, among other things for conventional level determination, and the apparatus according to the invention as in the embodiment of FIG. 6, can be adapted with advantage to be introduced into such existing tubes or ducts. The apparatus will then still make possible conventional level determination as just mentioned.

The cross-sectional view of FIG. 6 shows an outer or surrounding protective tube 64 of steel, i.e. an electrically conductive material. Inside this there is shown a nonconductive tube 63A, 63B having an internal partition 62. Preferably this is substantially planar as will appear from FIG. 6, but apparently can have other geometrical shapes when seen in cross-section. The major part of the tube cross-section within the wall 63A is here adapted to receive the liquid 6 the level of which is to be measured. With fluid-tight separation therefrom by means of partition 62 in the other part of the tube cross-section, there is provided an electrode 60 on a circuit board 69 so that the electrode is located close to or in contact with the adjacent side of partition 62. At the opposite side of circuit board 69 there is shown an oscillator 65 and an temperature circuit 67, corresponding to components or elements that have been discussed also on connection with preceding embodiments. An essential feature in the structure of FIG. 6 is the connecting lead 61 through circuit board 69 from electrode 60 to oscillator circuit 65. In this manner lead 61 will be very short, typically 2 mm, corresponding to a normal thickness of circuit boards.

What is important with the non-conductive tube 63A, 63B, 62 is that the electrode-oscillator probe with associated electronics is held separated in a fluid-tight manner from the liquid 6 being subject to measurement. For this purpose it is not required to have a specific and somewhat complicated cross-sectional profile as tube 63A, 63B, 62, since there may contemplated a modified and simpler solution with a single more or less half moon-shaped tube cross-section that either serves to contain the probe and the electronics, or to contain the liquid 6.

With the conductive and surrounding tube 64 which besides is grounded, there is present in this embodiment a well-defined counter-electrode which cooperates with electrode 60. Between these two electrodes the liquid 6 or possibly air or a gas above the liquid level, will constitute a dielectric that influences the capacitance of the measuring capacitor and thereby the output signal or signals being delivered.

Figure 7:
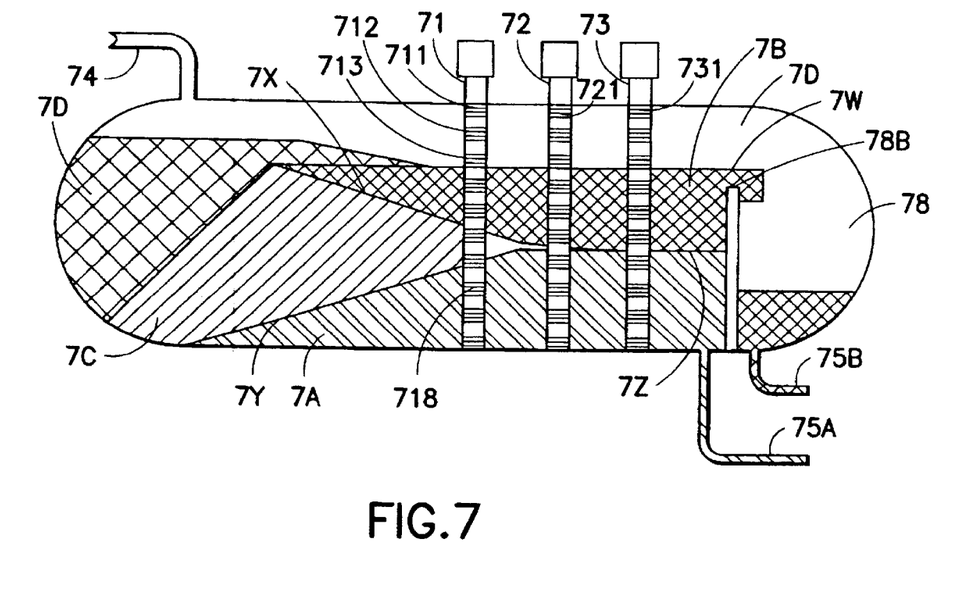
FIG. 7 shows a schematic vertical section in the form of a separation or sedimentation tank in which there are installed three separate rows of electrode-oscillator devices according to the invention for measuring interface levels between different fluids in the tank, FIG. 8 additionally shows a specific embodiment of the apparatus according to the invention in vertical section, for the purpose of measuring a level or an interface between two surrounding fluids.

Also FIG. 7 shows an example of measurement of levels or interfaces in a tank, based on a tube structure of the apparatus, but where the tube apparatus or devices are adapted to be surrounded by the media concerned in the form of liquids or fluid in general. This type of device applies particularly to tanks used for separating water and oil being produced from structures underneath the seabed.

In FIG. 7 there is shown a tank with an inlet 74 for unprocessed crude oil product, and an outlet 75A for water and an outlet 75B for oil. In the tank from the inlet end at 74 there will take place a separation in a common way under the influence of gravitation, so that there is built up a lower water layer 7A and an upper oil layer 7B flowing over a threshold 78B to an outlet chamber 78 in which the oil outlet 75B is located. In the vicinity of inlet 74 there is shown a region 7D of the tank contents that can constitute a foam-like mixture of the ingredients, these being separated more and more in a direction to the right in the figure of drawings. Normally, there will exist a transition or intermediate region 7C where oil and water can be present in a form of emulsion. Then follow the more separated regions 7A and 7B for water and oil respectively. Above the liquid surfaces there is a space or region 7D containing a gas phase with an interface or boundary 7W between the oil 7B and the gas space 7D. Other interfaces or boundaries are shown at 7Z between separated oil and water, at 7X and 7Y respectively between oil and water at one hand and the emulsion region 7C contiguous thereto. In such a tank it would be of high interest to measure where the respective interfaces are positioned, since the number of such interfaces can vary depending on the constituents being present and how these are separated.

In accordance with the invention the tank shown in FIG. 7 is equipped with three measuring devices generally denoted 71, 72 and 73, based on tube structures as mentioned, these being suitably here called carrier tubes. Each of the carrier tubes 71, 72 and 73 has a number of electrode-oscillator probes distributed over the major part of their length, preferably from the bottom of the tank and up to the top thereof, as it is indicated particularly for carrier tube 71 with probes 711, 712, 713 and further down towards the bottom a probe 718. An uppermost probe 721 and 731 are the only ones being indicated in the two other carrier tubes 72 and 73. An important point in such an arrangement is that the number of electrodes for each carrier tube is substantially larger than and preferably several times as large as the number of interface levels it is desired to measure. In all circumstances such probes will be positioned at mutual spacings chosen also with due consideration of desired resolution in the level measurements.

Figure 8:
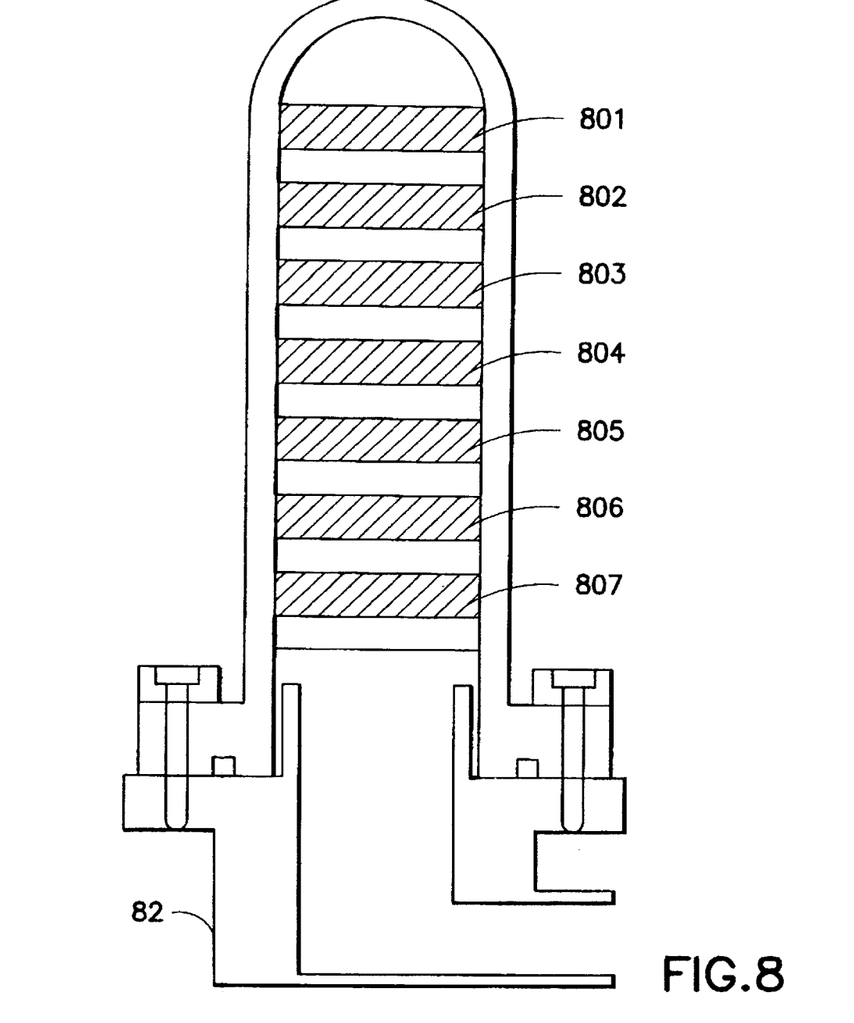
Figure 9:
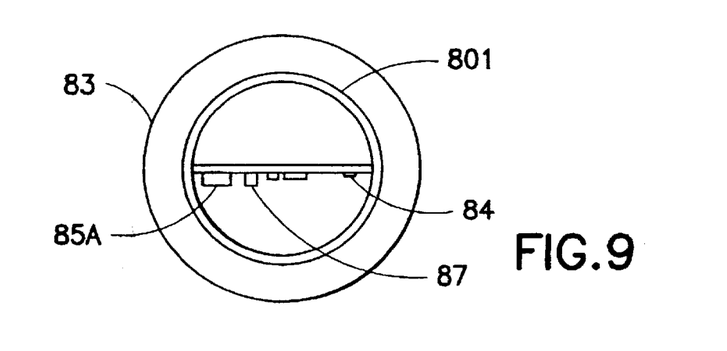
Figure 10:
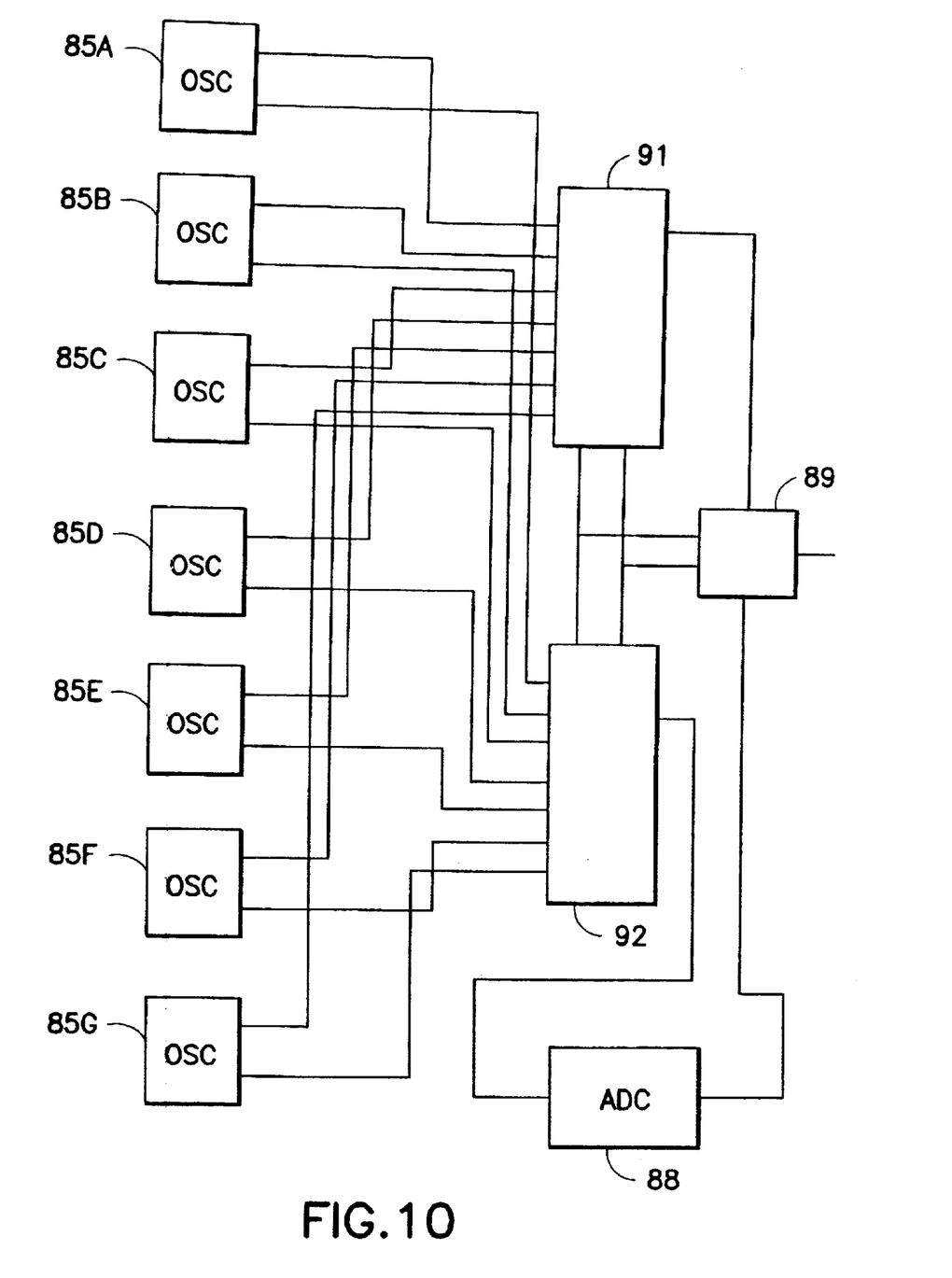

FIGS. 8, 9 and 10 show additionally a particular embodiment that in certain respects can be related to the one in FIG. 7. In a liquid- and pressure-tight housing 83 of tubular shape, there is internally provided electrodes 801–807 lying in parallel planes. These planes are preferably horizontal for the purpose of a vertical orientation of the whole apparatus, i.e. housing 83, in the case of level measurement. Quite in general at 82 in FIG. 8 there is indicated a supporting structure incorporated in the equipment being associated with the measurement. Here there can e.g. be the question of subsea measurement of oil leakage being entrapped underneath a roof-like cover, so that it is the interface between water and possible collected oil above the water surface, that is to be detected or measured.

FIG. 9 shows a cross-section of the apparatus of FIG. 8, with the tubular housing 83 and electrode 801 internally around the circumference of the housing. Diametrically in the internal cavity there is shown a supporting plate 84 with components incorporated and corresponding to previously described components, i.e. an oscillator circuit 85A and a temperature circuit 87.

A corresponding block diagram is shown in FIG. 10, where seven oscillator circuits 85A–85G correspond to electrodes 801–807 in FIG. 8, and are closely connected each to one of these. Moreover, FIG. 10 shows common selector circuits 91 and 92, an analog-digital converter 88 and an out-put unit 89 corresponding to the previously described arrangements.

The block diagram of FIG. 10 can, like the one in FIG. 5, also be taken as a basis for each measuring device in the respective carrier tubes 71, 72 and 73 in FIG. 7.

Figure 11:
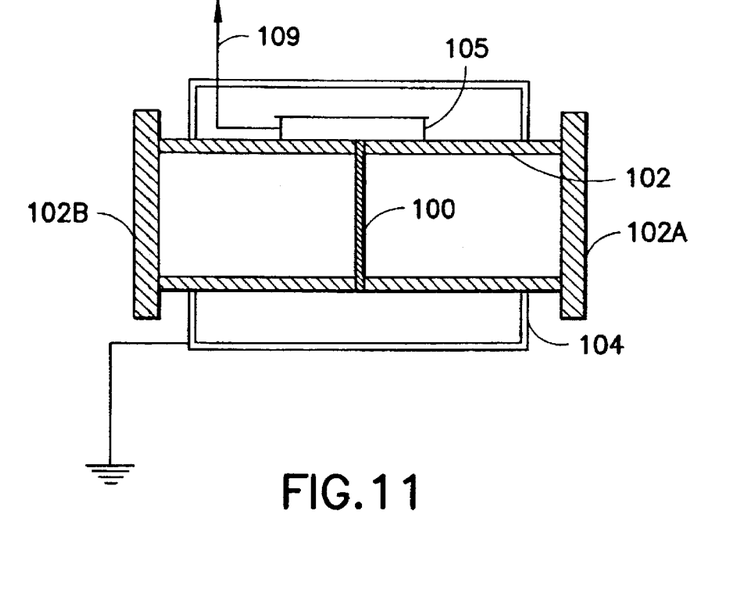

Finally FIG. 11 shows an embodiment according to the invention intended for detection or measurement of flowing fluids, e.g. in a pipeline or a processing plant or the like. In FIG. 11 there is shown a pipe length 102 made e.g. of composite materials, i.e. an electrically non-conductive material, and provided with flanges 102A and 102B for insertion in the pipeline or plant unit concerned. Externally of or encased in the tube wall 102 there is shown an electrode 100 running around the whole circumference of the pipe length. In close relationship to the electrode there is shown an oscillator circuit 105 that additionally can be considered to contain other components as discussed in connection with the preceding embodiments. From oscillator 105 there is schematically shown an output 109. Further there is shown a surrounding screen or encapsulation 104 of electrically conductive material. This screen covers a portion of the length of pipe 102 at either side of electrode 100 with associated oscillator circuit 105, and lies at a certain radial spacing outside pipe length 102. The function of such an apparatus will be understood in view of what is already explained above. This also will apply when the fluids flowing through the pipe length comprise several phases, mixtures of fluids or the like. The purpose of the apparatus can be either to determine whether certain liquids are present or not, or to determine how are the level relationships in the flow.

In addition to the relatively numerous variants of embodiments described above with reference to the drawings, it is obvious that the basic solution according to the invention makes possible additional practical embodiments. One such possibility for example consists in the detection of persons or bodies moving or being located in a space or delimited area, e.g. when passing through a door opening. Temperature compensation and a temperature measuring signal as mentioned, can also advantageously be utilized not only in that a single temperature-sensitive resistor (RT3 in FIG. 1) serves for compensation of both the temperature variation of oscillator components and for the temperature-dependent dielectric constant, but also by permitting a separate temperature measurement, that can be of interest per se in many cases of measurement. Without being explained more closely it will be obvious to experts in the field that suitable programming of the microprocessor or computer described, being connected to the apparatus, can provide for specific results or forms of signal processing that according to the circumstances can be of great value in utilizing the invention. Available technology and methods at this point and also with respect to components and materials being used in the apparatus, represent as a whole a wide spectre of practical possibilities being offered by the present invention.

What is claimed is:

1. An apparatus for detection or measurement of a medium using electrical capacitance, comprising:
    at least one electrode, wherein a capacitance to be measured is between said at least one electrode and a counter-electrode and said capacitance is of a medium being measured or detected;
    a lead conductor for connecting the at least one electrode to an associated LC-oscillator circuit, said conductor having a substantially smaller capacitance than a capacitance of the at least one electrode;
    the associated LC-oscillator circuit being comprised of an air coil and being operative for generating an output frequency which is a function of the capacitance associated with the at least one electrode and a dielectric constant of the medium, said output frequency being taken as a basis for the detection or measurement;
    a temperature sensing element for generating a temperature measuring signal to provide for temperature compensation;
    an analog-digital converter for receiving the temperature measuring signal and for outputting a corresponding digital temperature signal;
    a frequency counter for receiving the output frequency and for outputting a corresponding digital frequency signal to a microprocessor; and
    a microprocessor for receiving the digital temperature signal and the digital frequency signal and for computing a detection or measurement signal using the digital frequency signal and the digital temperature signal.

2. The apparatus according to claim 1, further comprising:
    an electrically screening encapsulation for surrounding at least the at least one electrode, the lead conductor, and the oscillating circuit, said encapsulation comprising:
        an electrically conductive portion; and
        an electrically non-conductive portion;
    wherein the at least one electrode is applied to an internal surface of the electrically non-conductive portion;
    wherein the counter-electrode comprises an environment of the medium (ground) and the electrically conductive portion of the encapsulation; and
    wherein the capacitance between the at least one electrode and the electrically conductive portion of the encapsulation is substantially smaller than the capacitance between the at least one electrode and ground.

3. The apparatus according to claim 1, wherein the temperature sensing element has good thermal contact with the air core coil to provide for temperature compensation of the LC-oscillator circuit.

4. The apparatus according to claim 1, wherein a focus of the measurement or detection is a water content of the medium, and wherein a fundamental frequency of the LC-oscillator circuit is within a range of frequencies where water has a pronounced minimum in its loss factor.

5. The apparatus according to claim 1, wherein the LC-oscillator circuit is frequency calibrated with one of air and water as a dielectric for the at least one electrode.

6. The apparatus according to claim 1, wherein the at least one electrode is formed at one side of a circuit board and the LC-oscillator circuit is located proximate the other side of the circuit board with said lead conductor arranged therethrough.

7. The apparatus according to claim 1, wherein the electrically non-conducting portion has a thickness of an order of magnitude comparable to a surface extent of the electrode.

8. The apparatus according to claim 1, further comprising:
    a measuring vessel for receiving the medium, said measuring vessel being comprised of electrically non-conductive material;
    a screen comprised of electrically conductive material;
    wherein the at least one electrode encircles the measuring vessel at the level of and at a given spacing from the medium therein; and
    wherein the at least one electrode is at least laterally surrounded by the screen of electrically conductive material, said screen having a distance from the at least one electrode larger than said given spacing.

9. The apparatus according to claim 8, further comprising:
    a cylinder of electrically non-conductive material with an internal cavity adapted to accommodate the measuring vessel;
    wherein the at least one electrode is in the form of a ribbon on an external circumference of the cylinder.

10. The apparatus according to claim 1, further comprising:
    an encapsulation having an electrically non-conductive front pointed part and an electrically conductive rear part, said front part being pointed for insertion into the medium;
    wherein the at least one electrode is rod- or thread-shaped and located centrally along the axis of the pointed front part of the encapsulation, where the at least one electrode is substantially surrounded by electrically non-conductive materials; and wherein the LC-oscillator circuit is located in the rear part of the encapsulation.

11. The apparatus according to claim 1, wherein the at least one electrode comprises a plurality of electrodes arranged in a vertically oriented column to measure or detect at least one liquid and each of said plural electrodes has its own LC-oscillator circuit directly associated therewith.

12. The apparatus according to claim 11, wherein the microprocessor is adapted to provide for frequency calibration with respect to each of the plural electrodes with associated LC-oscillator circuit, depending on whether said each electrode is fully immersed in a liquid or as a whole is located above the liquid level thereof.

13. The apparatus according to claim 11, wherein outputs from the associated LC-oscillator circuits of the plural electrodes are connected to at least one selector circuit for controlling activation of each of the plural electrodes during a measuring procedure.

14. The apparatus according to claim 11, further comprising:
a tube of electrically non-conductive material which is designed so that the plural electrodes with associated LC-oscillator circuits are separated in a liquid-tight manner from the liquid whose level is to be measured.

15. The apparatus according to claim 14, wherein the plural electrodes lie substantially in engagement with one side of the planar partition.

16. The apparatus according to claim 14, wherein the non-conductive tube is surrounded by a tube of electrically conductive material.

17. The apparatus according to claim 11, wherein the at least one liquid comprises different fluids in a tank, further comprising:
at least one vertically oriented carrier tube for detecting at least one boundary between the different fluids in the tank, said at least one carrier tube carrying a plurality of probes in a column, where each of said plural probes comprises an electrode and its LC-oscillator circuit;
wherein a number of plural probes being carried by each of the at least one carrier tube is substantially larger than a number of the at least one boundary to be measured.

18. The apparatus according to claim 11; further comprising:
a vertically tubular housing of electrically non-conductive material, said tubular housing containing the plural electrodes in the form of ribbons lying generally in parallel horizontal planes;
wherein the at least one liquid to be detected or a level of which is to be measured contacts the housing externally.

19. The apparatus according to claim 1, further comprising:
a pipe segment of electrically non-conductive material through which a fluid flow passes, said pipe segment having the at least one electrode provided around a circumference of the pipe segment; and
an electrically conductive screen disposed at a radial spacing outside the pipe segment, said screen surrounding the at least one electrode and associated LC-oscillator circuit.

20. The apparatus according to claim 1, wherein the medium being measured or detected is a flowing fluid, further comprising:
a pipe length of electrically non-conductive material, through which the flowing fluid passes, wherein the at least one electrode is arranged around the circumference of said pipe length; and
an electrically conductive screen disposed outside the pipe length surrounding the at least one electrode and the associated LC-oscillator circuit.

21. The apparatus according to claim 14, further comprising:
a planar partition incorporated in the tube for separating the plural electrodes in a liquid-tight manner from the liquid whose level is to be measured.

22. The apparatus according to claim 17, wherein the different fluids in the tank comprise at least one of oil, water, and a mixture of oil and water.

23. The apparatus according to claim 17, wherein a number of the plural probes being carried by each of the at least one carrier tube is several times the number of the at least one boundary to be measured.

24. The apparatus according to claim 1, wherein the medium comprises at least one of a fluid, a gas, and a solid.

25. The apparatus according to claim 1, wherein an effective spacing of the at least one electrode from the counter-electrode is of at least a similar order of magnitude than a surface area of the at least one electrode.

26. The apparatus according to claim 1, wherein the counter-electrode comprises an environment of the medium.

27. The apparatus according to claim 1, wherein the relationship of the lead conductor having a substantially smaller capacitance than the capacitance of the at least one electrode is maintained regardless of the medium.

28. The apparatus according to claim 1, wherein the relationship of the lead conductor having a substantially smaller capacitance than the capacitance of the at least one electrode is implemented by making a length of the lead conductor substantially smaller than a surface area of the at least one electrode.

29. The apparatus according to claim 1, further comprising:
an output device for receiving the computed detection or measurement signal from the microprocessor, said output device being one of an alarm, a recording, and a display device.

30. An apparatus for detection or measurement of a medium using electrical capacitance, comprising:
at least one electrode, wherein a capacitance to be measured is between said at least one electrode and a counter-electrode and said capacitance is of a medium being measured or detected; and
a lead conductor for connecting the at least one electrode to an associated oscillator circuit, said conductor having a substantially smaller capacitance than a capacitance of the at least one electrode;
the associated oscillator circuit being operable for generating an output frequency that is a function of the capacitance associated with the at least one electrode and a dielectric constant of the medium, said output frequency being used as a basis for the detection or measurement.

31. The apparatus according to claim 30, wherein the medium comprises at least one of a fluid, a gas, and a solid.

32. The apparatus according to claim 30, wherein an effective spacing of the at least one electrode from the counter-electrode is of at least a similar order of magnitude than a surface area of the at least one electrode.

33. The apparatus according to claim 31, wherein the counter-electrode comprises an environment of the medium.

34. The apparatus according to claim 32, wherein the relationship of the lead conductor having a substantially smaller capacitance than the capacitance of the at least one electrode is maintained regardless of the medium.

35. The apparatus according to claim 30, wherein the relationship of the lead conductor having a substantially smaller capacitance than the capacitance of the at least one electrode is implemented by making a length of the lead conductor substantially smaller than a surface area of the at least one electrode.

36. The apparatus according to claim 30, further comprising:
a temperature compensation unit for compensating for an effect of an ambient temperature on the oscillating circuit.

37. The apparatus according to claim 30, further comprising:
a temperature compensation unit for compensating for an effect of an ambient temperature on the oscillator circuit.

38. The apparatus according to claim 30, further comprising:
a microprocessor for receiving the output frequency and for computing a detection or measurement signal using the output frequency.

39. The apparatus according to claim 30, further comprising:
a microprocessor for receiving the output frequency and for computing a detection or measurement signal using the output frequency; and
a temperature measurement unit for compensating for an effect of an ambient temperature on the oscillator circuit, said temperature measurement unit sending a temperature measurement to a microprocessor;
the microprocessor being operable for receiving the output frequency and the temperature measurement and for computing a detection or measurement signal using the received output frequency and the received temperature measurement.

40. The apparatus according to claim 30, wherein the oscillator circuit comprises an LC circuit.

41. The apparatus according to claim 34, wherein the LC circuit comprises an air core coil.

42. The apparatus according to claim 40, further comprising:
a temperature-dependent resistor which is physically located in close thermal contact with the air core coil, said temperature-dependent resistor compensating for an effect of an ambient temperature on the oscillator circuit.

43. An apparatus for detection or measurement of a medium using electrical capacitance, comprising:
at least one electrode, wherein a capacitance to be measured is between said at least one electrode and a counter-electrode and said capacitance is of a medium being measured or detected;
a lead conductor for connecting the at least one electrode to an associated LC-oscillator circuit, said conductor having a substantially smaller capacitance than a capacitance of the at least one electrode;
the associated LC-oscillator circuit comprising an air coil and being operative for generating an output frequency which is a function of the capacitance associated with the at least one electrode and a dielectric constant of the medium, said output frequency being taken as a basis for the detection or measurement;
a temperature sensing element having good thermal contact with the air core coil for generating a temperature measuring signal to provide for temperature compensation of the LC-oscillator;
an analog-digital converter for receiving the temperature measuring signal and for outputting a corresponding digital temperature signal;
a frequency counter for receiving the output frequency and for outputting a corresponding digital frequency signal to a microprocessor; and
a microprocessor for receiving the digital temperature signal and the digital frequency signal and for computing a detection or measurement signal using the digital frequency signal and the digital temperature signal.

* * * * *